US007960582B2

(12) United States Patent
Blixt et al.

(10) Patent No.: US 7,960,582 B2
(45) Date of Patent: Jun. 14, 2011

(54) PROCESS FOR THE PREPARATION AND RESOLUTION OF MANDELIC ACID DERIVATIVES

(75) Inventors: Hans Jorgen Blixt, Sodertalje (SE); Bo Lars Gustaf Bosson, Sodertalje (SE); Roberto Guiseppe Paolo Gatti, Sodertalje (SE); Simone Zaramella, Sodertalje (SE); Michael William Senior, Macclesfield (GB); Kurt Vogtli, Aarau (CH); Andrea Zistler, Aarau (CH)

(73) Assignee: AstraZeneca AB, Sodertalje (SE)

( * ) Notice: Subject to any disclaimer, the term of this patent is extended or adjusted under 35 U.S.C. 154(b) by 745 days.

(21) Appl. No.: 10/579,854

(22) PCT Filed: Nov. 25, 2004

(86) PCT No.: PCT/GB2004/004964
§ 371 (c)(1),
(2), (4) Date: Jul. 21, 2008

(87) PCT Pub. No.: WO2005/054168
PCT Pub. Date: Jun. 16, 2005

(65) Prior Publication Data
US 2008/0312457 A1 Dec. 18, 2008

(30) Foreign Application Priority Data
Nov. 28, 2003 (SE) ........................................ 0303220

(51) Int. Cl.
*C07C 59/48* (2006.01)
(52) U.S. Cl. ........................................................ 562/470
(58) Field of Classification Search .................... 562/470
See application file for complete search history.

(56) References Cited

U.S. PATENT DOCUMENTS

| 1,867,274 | A | * | 7/1932 | Manske | 562/470 |
| 4,198,524 | A | * | 4/1980 | Tashiro et al. | 562/470 |
| 4,239,912 | A | * | 12/1980 | Halmos | 562/401 |
| 4,259,521 | A | * | 3/1981 | Kazan et al. | 562/401 |
| 4,260,815 | A | * | 4/1981 | Kazan et al. | 562/401 |
| 7,129,233 | B2 | | 10/2006 | Inghardt et al. | 514/210.02 |
| 7,645,751 | B2 | | 1/2010 | Inghardt et al. | 514/210.02 |
| 7,803,954 | B2 | | 9/2010 | Inghardt et al. | 548/952 |
| 2008/0293965 | A1 | | 11/2008 | Bosson et al. | 562/470 |
| 2008/0319206 | A1 | | 12/2008 | Al-Saffar et al. | 548/953 |
| 2010/0087651 | A1 | | 4/2010 | Inghardt et al. | 546/268.1 |

FOREIGN PATENT DOCUMENTS

| EP | 1236714 | 9/2002 |
| JP | 1221345 | 9/1989 |
| JP | 2001072644 | 3/2001 |
| WO | WO 02/44145 A | 6/2002 |
| WO | WO 02/068391 A | 9/2002 |
| WO | WO 2005/054168 | 9/2002 |
| WO | WO 2006/090153 | 8/2006 |
| WO | WO 2006/125964 | 11/2006 |

OTHER PUBLICATIONS

Samuel H. Wilen, Tables of Resolving Agents and Optical Resolutions (Edited by Ernest L. Eliel), 1972, pp. 18-23, 49-78, & 121-131.*
Michael B. Smith & Jerry March, March's Advanced Organic Chemistry (5th edition) 2001, pp. 151-155 & 199-202.*
Ebbers et al. "Controlled racemization and asymmetric transformation of α-substituted carboxylic acids in the melt" Tetrahedron: Asymmetry 10(19): 3701-3718 (1999).
Ebbers et al. "New resolving bases for ibuprofen and mandelic acid: qualification by binary phase diagrams" Tetrahedron: Asymmetry 8(24): 4047-4057 (1997).
Hoover et al. "Semisynthetic cephalosporins. Synthesis and structure-activity relationships of 7-mandelamido-3-cephem-4-carboxylic acids" J. Med. Chem. 17(1):34-41 (1974).
Nieuwenhuijzen et al. "The role of nucleation inhibition in optical resolutions with families of resolving agents" Angew. Chem. Int. Ed. 41(22):4281-4286 (2002).

* cited by examiner

*Primary Examiner* — Jason M Nolan
(74) *Attorney, Agent, or Firm* — Morgan Lewis & Bockius LLP

(57) ABSTRACT

The present invention relates to a new process for the resolution of mandelic acid derivatives from racemic mandelic acid derivative mixtures by salt formation with chiral base cyclic amides; to the resolved mandelic acid cyclic amide salts (see, for example, formula IIa), as well as certain other metal and amine salts of the mandelic acid derivatives, and to the use of the resolved mandelic acid derivatives as intermediates suitable for large-scale manufacturing of, for example, pharmaceutical compounds; Formula IIa, wherein R is selected from $CHF_2$, H, C1-6 Alkyl, $CH_2F$, $CHCl_2$ and $CClF_2$; and wherein n is 0, 1 or 2; R1 is H or C1-6 Alkyl and X is H, halo or C1-6 Alkyl.

8 Claims, No Drawings

PROCESS FOR THE PREPARATION AND RESOLUTION OF MANDELIC ACID DERIVATIVES

FIELD OF THE INVENTION

The present invention relates to a new process for the preparation and resolution of mandelic acid derivatives from racemic mandelic acid derivative mixtures, by salt formation with chiral base cyclic amides. The invention also relates to mandelic acid derivative cyclic amide salts, to certain other metal and amine salts of mandelic acid derivatives, as well as to the use of the resolved mandelic acid derivatives as intermediates suitable for large-scale manufacturing of, for example, pharmaceutical compounds.

BACKGROUND

Various amines have been reported as resolving agents for mandelic acid derivatives. For the resolution of mandelic acids a number of chiral amines have been described, e.g. α-methylbenzylamine, 2-benzylamino-1-butanol, (R)-2-tert-butyl-3-methylimidazolidin-4-one (BMI), (+)-cinchonine, brucine, quinine, quinidine, (−)-ephedrine, (−)-2-amino-1-butanol, amphetamine and adrenaline. These amines as well as others are described in E. J. Ebbers et al. *Tetrahedron: Asymmetry* 1997, 8, 4047-4057 and references cited therein.

In J. Hoover et al., (*J. Med. Chem.* 1974, 17, 34-41) are disclosed 21 substituted mandelic acids with references to original literature. The described resolving bases are (−)-ephedrine, brucine and (+)-α-methylbenzylamine.

J. Nieuwenhuijzen et al. (*Angew. Chem. Int. Ed.* 2002, 41, 4281-4286) describes the resolution of 4-chloromandelic acid with α-methylbenzylamine with or without a 1:1 ortho: para mixture of nitro-substituted α-methylbenzylamine (10 mol %).

JP2001072644 describes optical resolution of 2-chloromandelic acid with N-benzyl-α-methylbenzylamine and derivatives thereof. JP 1221345 describes optical resolution of phenyl-substituted mandelic acid derivatives with amino acid hydrazines.

However, there remains a need for further means for resolving mandelic acid derivatives. Mandelic acids are used in the manufacture of a range of interesting molecules, such as pharmaceuticals. Thus, the invention also relates to the use of the resolved mandelic acid derivatives as intermediates suitable for large-scale manufacturing of, for example pharmaceutical compounds, e.g. compounds as described in WO 02/44145.

A number of bases, including such described in the art, were tested in order to obtain acceptable resolution of mandelic acid derivatives (particularly 3-chloro-5-difluoromethoxymandelic acid), e.g. α-methylbenzylamine, (S)-1-naphthylethylamine, (+)-cinchonine, (+)-dihydroabietylamine, (S)-2-amino-2-phenylethanol, (−)-ephedrine, L-phenylalaniole, and α,α-diphenyl-D-prolinole. None of these yielded particularly satisfactory results for large-scale manufacturing purposes (having low yield and low enantiomeric excess). By large-scale we include manufacture of Kg quantities of material.

We have now surprisingly found that racemic mandelic acid derivatives may be resolved by salt formation with chiral base cyclic amides, such as proline amide.

We have also surprisingly found certain metal salts, and certain amine salts of mandelic acid derivatives (particularly (R)-3-chloro,5-difluoro-methoxy mandelic acid) which have desirable characteristics and are useful in manufacturing processes—see Example 12 and claims hereinafter.

DESCRIPTION OF THE INVENTION

Accordingly, there is provided a process for resolving (R)- or (S)-optionally substituted mandelic acids from racemic mixtures of said optionally substituted mandelic acids by salt formation with a chiral base (D)- or (L)-cyclic amide, comprising the steps: forming a mixture in a solvent, or mixture of solvents, of a racemic, optionally substituted, mandelic acid; and a chiral base (D)- or (L)-cyclic amide, wherein the chiral base used is either (D) for separation of (R)-mandelic acids, or (L) for separation of (S)-mandelic acids, at an acid:base molar ratio of 1:0.25-0.75; and wherein the solvent, or mixture of solvents, may optionally contain water in the range of 5 to 15% (vol.) of solvent; and (b) separating the respective (R)/(D) or (S)/(L) mandelic acid-cyclic amide salt. According to a further aspect of the invention, there is provided a process for resolving (R)- or (S)-substituted mandelic acids from racemic mixtures of said substituted mandelic acids by salt formation with a chiral base (D)- or (L)-cyclic amide as described hereinbefore and hereinafter.

It is to be understood that said "(R)- or (S)-optionally substituted mandelic acids" may be as described in WO 02/44145, and wherein said definitions and disclosed optionally substituted mandelic acids are incorporated into this specification by reference.

It is also to be understood that said "(R)- or (S)-substituted mandelic acids" may be those mandelic acid fragments of the molecules described in WO 02/44145, and wherein said definitions and disclosed substituted mandelic acids are incorporated into this specification by reference. Also incorporated into this specification by reference are details and examples of preparation of such substituted mandelic acids described in WO 02/44145 (for example, Example 1 therein).

A general outline of the process is as follows (wherein R, $R_1$, X and n are as defined herein):

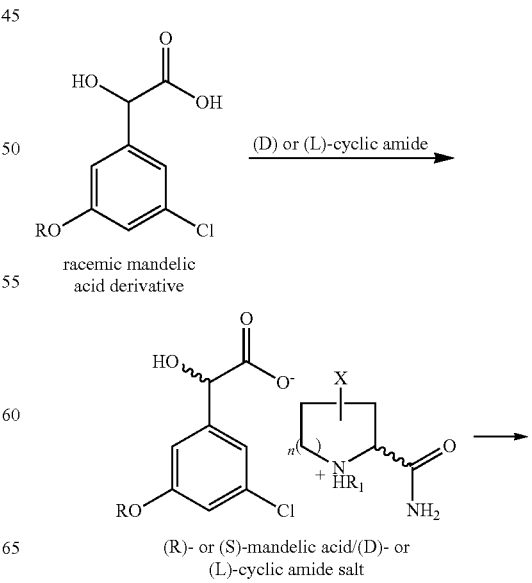

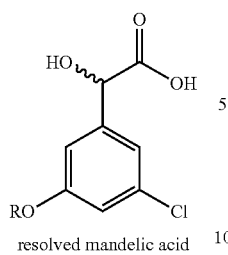

resolved mandelic acid

In the above scheme, preferably $R_1$ and X are both H.

In this specification, unless otherwise stated, the term "cyclic amide" includes optionally substituted forms thereof and includes, but is not limited to, proline amide, azetidine-2-carboxamide and piperidine-2-carboxamide as well as substituted forms thereof. Substitution may be on a ring nitrogen atom, by $C_{1-6}$ Alkyl, or on a suitable ring carbon atom by $C_{1-6}$ Alkyl or halo (for example, chloro, fluoro or bromo). Unsubstituted cyclic amides are preferred, but when substituted, substitution on a ring nitrogen atom or mono-substitution on a suitable ring carbon atom is preferred.

In this specification it is to be understood that, unless stated otherwise, when a (D) or (L) cyclic amide salt is drawn (as for example in formula II) then the cyclic amide may be optionally substituted on the nitrogen atom by $C_{1-6}$ Alkyl, or on a suitable ring carbon atom by $C_{1-6}$ Alkyl or halo (such as fluoro, chloro or bromo) as shown in formula I(x) below (wherein n is 0, 1 or 2; $R_1$ is H or $C_{1-6}$ Alkyl and X is H, halo or $C_{1-6}$ Alkyl) . . .

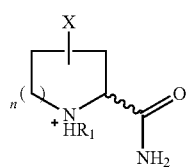

I(x)

In this specification it is to be understood that an optionally substituted (D) cyclic amide as described herein has the (2R) stereochemistry shown in formula I(y) below (wherein n is 0, 1 or 2; $R_1$ is H or $C_{1-6}$ Alkyl and X is H, halo or $C_{1-6}$ Alkyl).

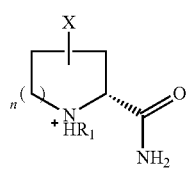

I(y)

In this specification it is to be understood that an optionally substituted (L) cyclic amide as described herein has the (2S) stereochemistry shown in formula I(z) below, (wherein n is 0, 1 or 2; $R_1$ is H or $C_{1-6}$ Alkyl and X is H, halo or $C_{1-6}$ Alkyl).

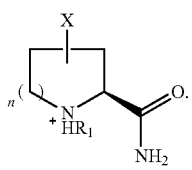

I(z)

It is to be understood that all isomers within the definitions of chiral base cyclic amide disclosed herein are covered by the invention.

For the avoidance of doubt it is to be understood that in this specification '$C_{1-6}$' means a carbon group having 1, 2, 3, 4, 5 or 6 carbon atoms.

In this specification, unless stated otherwise, the term "alkyl" includes both straight and branched chain alkyl groups and may be, but is not limited to, methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl.

According to another aspect of the invention there is provided a process for resolving (R)- or (S)-substituted mandelic acids from racemic mixtures of said substituted mandelic acids by salt formation with a chiral base (D)- or (L)-cyclic amide, comprising the steps:

(a) forming a mixture in a solvent, or mixture of solvents, of a racemic mandelic acid derivative of formula I;

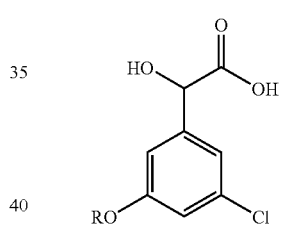

I wherein R is selected from $CHF_2$, H, $C_{1-6}$ Alkyl, $CH_2F$, $CHCl_2$ and $CClF_2$; and either a chiral base (D)-cyclic amide or (L)-cyclic amide of formula I(x) wherein n is 0, 1 or 2; $R_1$ is H or $C_{1-6}$ Alkyl and X is H, halo or $C_{1-6}$ Alkyl,

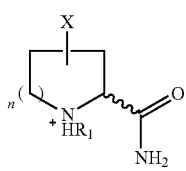

I(x)

wherein the chiral base used is either (D) for separation of (R)-mandelic acids, or (L) for separation of (S)-mandelic acids;

at an acid:base molar ratio of 1:0.25-0.75; and wherein the solvent, or mixture of solvents, may optionally contain water in the range of 5 to 15% (vol.) of solvent; and (b) separating the respective (R)/(D) or (S)/(L) mandelic acid-cyclic amide salt of formula IIa;

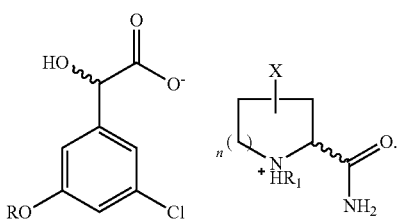

IIa

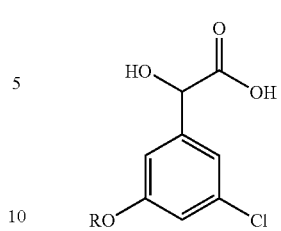

I

The amounts of racemic mandelic acid derivative and chiral base cyclic amide in step (a) of the processes are added at a molar ratio of 1:0.25-0.75; alternatively at a molar ratio of 1:0.4-0.7. In another aspect, a mandelic acid derivative:chiral base molar ratio of 1:0.48-0.52 is used (for example in ethyl acetate solvent), and in another aspect the molar ratio is 1:0.50. It is to be understood that the molar ratios also cover experimental variation around these limits, e.g. ±0.005.

In this specification, unless otherwise stated, the term "ethyl acetate" means ethyl acetate, which, however, may be replaced by another acetate, such as propyl acetate or butyl acetate. In general, (1-4C) acetates may be used.

Other solvents may also be used, and are suitable for the formation of (S)-3-chloro,5-difluoro-methoxy mandelic acid.L-prolinamide salt. These solvents include acetonitrile, acetone, 2-butanone (MEK, methyl ethyl ketone), 4-methyl-2-pentanone (MIBK, methyl isobutyl ketone), tert-butyl methyl ether (TBME), 2-propanol and ethanol. It is expected that these solvents can also be applied in formation of the (R)-3-chloro,5-difluoro-methoxy mandelic acid.D-prolinamide salt.

The above-mentioned solvents may be used as pure solvents, or as mixtures with other solvents from those mentioned above. Furthermore, the solvent or solvent mixture may optionally contain water (suitably in an amount from 5% to 15% v/v). A preferred solvent is ethyl acetate.

A further aspect of the invention provides a process for resolving (R)- or (S)-optionally substituted mandelic acids from racemic mixtures of said optionally substituted mandelic acids by salt formation with a chiral base (D)- or (L)-cyclic amide, comprising the steps:

(a) forming a mixture in ethyl acetate/water of a racemic optionally substituted mandelic acid; and a chiral base (D)- or (L)-cyclic amide, wherein the base used is (D) for separation of (R) acids, and (L) for separation of (S) acids, at an acid:base molar ratio of 1:0.48-0.52; and wherein the water is in the range of 5 to 15% (vol.) of ethyl acetate; then (b) heating and stirring said mixture at reflux; then (c) cooling said mixture/suspension from step (b), followed by filtering said cooled mixture/suspension to obtain the respective R/D or S/L mandelic acid cyclic amide salt.

According to another aspect of the invention there is provided a process for resolving (R)- or (S)-mandelic acid derivatives from racemic mandelic acid derivatives by salt formation with a chiral base (D)- or (L)-cyclic amide, comprising the steps:

(a) forming a mixture in ethyl acetate/water of a racemic mandelic acid derivative of formula I;

wherein R is selected from $CHF_2$, H, $C_{1-6}$ Alkyl, $CH_2F$, $CHCl_2$ and $CClF_2$; and a chiral base (D)- or (L)-cyclic amide wherein the base used is (D) for separation of (R) acids, and (L) for separation of (S) acids, at an acid:base molar ratio of 1:0.48-0.52; and wherein the water is in the range of 5 to 15% (vol.) of ethyl acetate; then (b) heating and stirring said mixture at reflux; then (c) cooling said mixture/suspension from step (b), followed by filtering said cooled mixture/suspension to obtain the respective (R)/(D) or (S)/(L) mandelic acid cyclic amide salt of formula II;

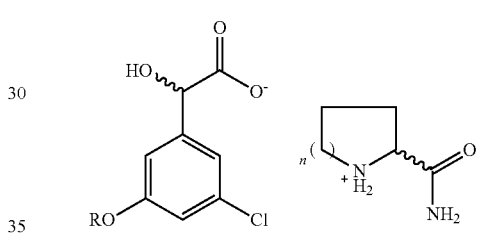

II wherein R is selected from $CHF_2$, H, $C_{1-6}$ Alkyl, $CH_2F$, $CHCl_2$ and $CClF_2$; and n is 0, 1 or 2.

In another aspect of the invention, there is provided a process for resolving (R)-mandelic acid derivatives from racemic mandelic acid derivatives by salt formation with a chiral base (D)-cyclic amide, comprising the steps:

(a) forming a mixture in ethyl acetate/water of a racemic mandelic acid derivative of formula I;

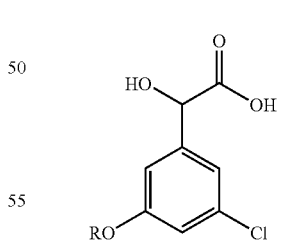

I wherein R is selected from $CHF_2$, H, $C_{1-6}$ Alkyl, $CH_2F$, $CHCl_2$ and $CClF_2$; and a chiral base (D)-cyclic amide, at an acid:base molar ratio of 1:0.48-0.52; and wherein the water is in the range of 5 to 15% (vol.) of ethyl acetate; then (b) heating and stirring said mixture at reflux; then (c) cooling said mixture/suspension from step (b), followed by filtering said cooled mixture/suspension to obtain a mandelic acid cyclic amide salt of formula III;

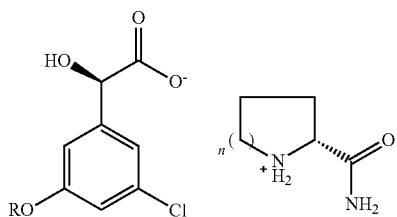

III

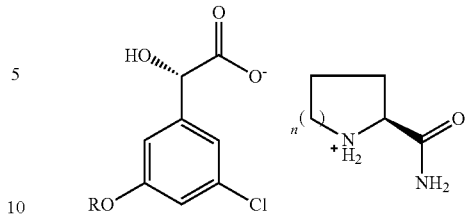

IV wherein R is selected from CHF$_2$, H, C$_{1-6}$ Alkyl, CH$_2$F, CHCl$_2$ and CClF$_2$; and n is 0, 1 or 2.

In one embodiment of this aspect there is provided a process wherein R of Formula III is CHF$_2$, and n of Formula III is 1, represented by Formula VI;

wherein R is selected from CHF$_2$, H, C$_{1-6}$ Alkyl, CH$_2$F, CHCl$_2$ and CClF$_2$; and n is 0, 1 or 2.

In one embodiment of this aspect, there is provided a process, wherein R of Formula IV is CHF$_2$, and n of Formula IV is 1, represented by Formula VII;

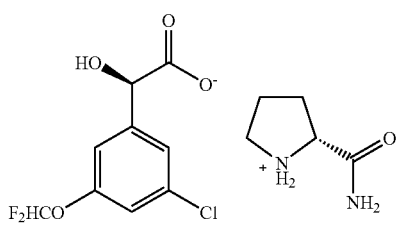

VI

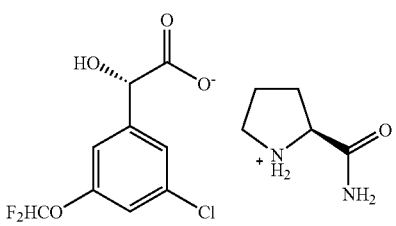

VII

In another aspect of the invention, there is provided a process for resolving (S)-mandelic acid derivatives from racemic mandelic acid derivatives by salt formation with a chiral base (L)-cyclic amide, comprising the steps:

(a) forming a mixture in ethyl acetate/water of a racemic mandelic acid derivative of formula I;

In another aspect of the invention, there is provided a process of the invention, wherein R of Formula I is CHF$_2$, represented by Formula V;

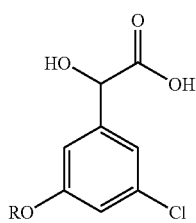

I

V wherein R is selected from CHF$_2$, H, C$_{1-6}$ Alkyl, CH$_2$F, CHCl$_2$ and CClF$_2$; and a chiral base (L)-cyclic amide, at an acid:base molar ratio of 1:0.48-0.52; and wherein the water is in the range of 5 to 15% (vol.) of ethyl acetate; then (b) heating and stirring said mixture to reflux; then (c) cooling said mixture/suspension from step (b), followed by filtering said cooled mixture/suspension to obtain a mandelic acid cyclic amide salt of formula IV;

In the above aspects and embodiments, the cyclic amide used may be optionally substituted on the nitrogen atom by C$_{1-6}$ Alkyl, or on a suitable ring carbon atom by C$_{1-6}$ Alkyl or halo (such as fluoro, chloro or bromo) as shown for formula I(x) above.

The racemic mandelic acid derivative/cyclic amide and solvent (for example, ethyl acetate) mixture in (a) of the processes may be heated to reflux, followed by addition of the water to obtain a suspension. This suspension is normally stirred at reflux for 10 minutes before starting the cooling process.

The racemic mandelic acid derivative/cyclic amide and solvent (for example, ethyl acetate) mixture in (a) of the processes may be optionally heated (for example, to reflux). The presence of water (in the range of 5 to 15% (vol.) of solvent) is preferred, and the optional heating of the mixture may be followed by addition of the water to obtain the suspension. This suspension is normally stirred at reflux for 10 minutes before cooling and separating the desired mandelic acid-cyclic amide salt.

The suspension in step (c) of the processes described herein may be cooled to 20 to 25° C. for 10 to 15 hours, followed by further cooling to 15 to 19° C. for additional 40 to 60 minutes. Preferably, the suspension is cooled to about 23° C. for 13 hours followed by further cooling to 18° C. for additional 45 minutes.

Alternatively, the suspension in (c) of the processes described herein is cooled to about 15 to 19° C. for 3 to 4 hours. Preferably, the suspension is cooled to 18° C. for 3 to 4 hours.

The added amount of optional water in step (a) in the processes is in the range of 5 to 15% (vol.) of ethyl acetate. This gives a solution wherein the concentration of water is 5 to 10% in ethyl acetate, e.g. 0.3 ml water added in 3.7 ml ethyl acetate is 7.5%. Preferably, the added amount of water is in the range of 5 to 10% (vol.) of ethyl acetate. Particularly preferred is when the added amount of water is in the range of 6 to 7% (vol.) of ethyl acetate.

The concentration of racemic mandelic acid derivative in the ethyl acetate and water solvent mixture is usually in the range of 0.5-2.5 mmol per ml of ethyl acetate and water. Preferably, the racemic mandelic acid derivative is added at a concentration range of 1.0-2.0 mmol per ml of ethyl acetate and water. Particularly preferred is when the racemic mandelic acid derivative is added at a concentration range of 1.0-1.2 mmol per ml of ethyl acetate and water.

The suspension comprising the salt obtained in step (c) of the processes described herein may be further washed with ethyl acetate. The salt may be dissolved in a mixture of HCl and ethyl acetate followed by separation of the organic layer and concentrating said organic layer to dryness to obtain resolved mandelic acid derivative. Preferably, the mixture of HCl and ethyl acetate is a 1:1 (vol.) mixture of 1M HCl and ethyl acetate. The resolved mandelic acid derivative may be analysed by conventional chiral HPLC techniques.

In another aspect of the invention there is provided a (R)/(D) or (S)/(L) mandelic acid cyclic amide salt having the formula II;

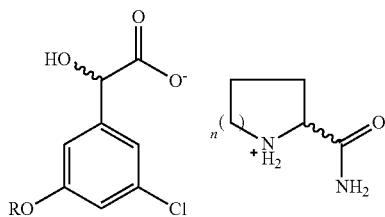

wherein R is selected from $CHF_2$, H, $C_{1-6}$ Alkyl, $CH_2F$, $CHCl_2$ and $CClF_2$; and n is 0, 1 or 2.

In one embodiment of this aspect there is provided a mandelic acid cyclic amide salt, represented by formula III;

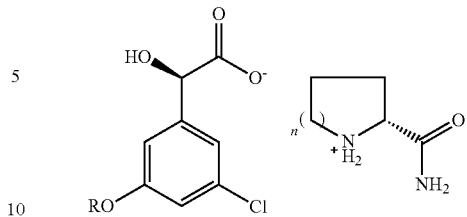

wherein R is selected from $CHF_2$, H, $C_{1-6}$ Alkyl, $CH_2F$, $CHCl_2$ and $CClF_2$; and n is 0, 1 or 2.

Preferably, said mandelic acid-cyclic amide salt is a mandelic acid-cyclic amide salt, wherein R is $CHF_2$, and n is 1, represented by Formula VI;

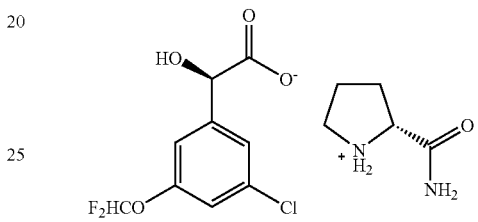

In the above aspects and embodiments, the cyclic amide used in the mandelic acid-cyclic amide salt may be optionally substituted on the nitrogen atom by $C_{1-6}$ Alkyl, or on a suitable ring carbon atom by $C_{1-6}$ Alkyl or halo (such as fluoro, chloro or bromo) as shown for formula I(x) above.

The said mandelic acid cyclic amide salts represented by the Formulas II, III and VI are obtainable by the processes of the present invention.

Also provided are the products obtainable by the processes described within this specification and within any of the Examples disclosed herein.

There is a need for a more convenient and more economically efficient process for the manufacturing of large scale quantities of high quality (pure) resolved mandelic acid derivatives, where factors like costs, manufacturing time, use of more environmentally friendly solvents etc. are vital for commercial application. The present invention provides for such a process. The processes of the invention uses an improved process for the manufacture of resolved mandelic acid derivatives in which non-expensive raw materials and thermally safe work up conditions are used to achieve these quality resolved mandelic acid derivatives ready to use in further chemical processing.

The invention further provides the use of a mandelic acid-cyclic amide salt according to the invention in the manufacture of pharmaceutical products; the use of a mandelic acid-cyclic amide salt according to the invention as chemical intermediates and the use of a mandelic acid cyclic amide salt according to the invention as chemical intermediates in manufacture of pharmaceutical products (for example for use in treating cardiovascular diseases).

The phrase "e.e." denotes an abbreviation for enantiomeric excess and is defined as the mole fraction denoting the enantiomers in a mixture:

% e.e.=[R]−[S]/[R]+[S]

where [R] and [S] are the concentrations of the (R)- and (S)-enantiomers. In a reaction a chiral compound is often obtained as a mixture of enantiomers. If, for example, 80% of the (R)-enantiomer is formed and 20% of the (S)-enantiomer then the e.e. is: 80−20/80+20=60%.

The present invention is described in more detail in the following non-limiting Examples.

EXAMPLES 1-3

In these Examples the following method was used, with volumes and amounts as outlined in Table 1.

The racemic mandelic acid derivative 3-chloro,5-difluoro-methoxy mandelic acid and (D)-proline amide were added to ethyl acetate saturated in water (8.1% water in ethyl acetate). The mixture was heated to reflux and stirred for 10 minutes at reflux. The thin suspension was cooled to 23° C. over 13 hours followed by further cooling to 18° C. over 40 minutes. The suspension was filtered and washed with ethyl acetate (3×30 ml) to give the salt. A sample was dissolved in a 1:1 mixture of 1 M HCl and ethyl acetate. The organic layer was separated, concentrated to dryness and analysed by chiral HPLC (for suitable methodology, see Example 11A). This showed a high degree of purity of the "correct" enantiomer (see Table 1), (R)-3-chloro,5-difluoro-methoxy mandelic acid.

TABLE 1

| Example no. | mmol MA[1] | mmol PA | Eq. PA | EtOAc (ml) | Water/EtOAc (%) | mmol MA/ml water-EtOAc | e.e. (%) |
|---|---|---|---|---|---|---|---|
| 1 | 1.16 | 0.57 | 0.49 | 0.97 | 8.1 | 1.20 | 84.2 |
| 2 | 1.16 | 0.57 | 0.49 | 0.51 | 8.1 | 2.27 | 95.3 |
| 3 | 1.09 | 0.53 | 0.49 | 0.67 | 8.1 | 1.63 | 90.6 |

MA = racemic mandelic acid derivative, 3-chloro,5-difluoro-methoxy mandelic acid.
PA = (D)-proline amide.
Eq. PA = Amount of equivalents of (D)-proline amide compared to racemic mandelic acid derivative.
EtOAc = ethyl acetate, as solution saturated in water.
Water/EtOAc (%) = concentration of water in ethyl acetate.
mmol MA/ml water-EtOAc = concentration range of racemic mandelic acid derivative per ml of ethyl acetate and water.
e.e. (%) = enantiomeric excess defined as the % mole fraction denoting the enantiomers in a mixture.
[1]Corrected for purity, i.e. initially 86% pure racemic mandelic acid derivative.

EXAMPLES 4-9

In these Examples the following method was used, with volumes and amounts as outlined in Table 2.

The racemic mandelic acid derivative 3-chloro,5-difluoro-methoxy mandelic acid and (D)-proline amide were added to ethyl acetate and the mixture heated to reflux. At reflux, water was added and the mixture was stirred for another 10 minutes at reflux. The thin suspension was allowed to cool to 18° C. over 3 hours (in Examples 4-8; 4 hours in Example 9). The suspension was filtered and washed with ethyl acetate (3×30 mil) to give the salt. The salt was dissolved in a 1:1 mixture of 1 M HCl and ethyl acetate. The organic layer was separated, concentrated to dryness and analysed by chiral HPLC (for suitable methodology, see Example 11A). This showed a high degree of purity of the "correct" enantiomer (see Table 2), (R)-3-chloro,5-difluoro-methoxy mandelic acid.

To exemplify in more detail, the following scheme was used in Example 6:

The racemic mandelic acid derivative 3-chloro,5-difluoro-methoxy mandelic acid (26.18 g, 93.3 mmol, 1 eq, 90% pure according to HPLC) and (D)-proline amide (4.80 g, 42 mmol, 0.45 eq) were added to ethyl acetate (54.5 ml) and the mixture heated to reflux. At reflux, 5.5 ml of water was added and the mixture stirred for another 10 minutes at reflux. The thin suspension was allowed to cool to 18° C. over 3 hours. The suspension was filtered and washed with ethyl acetate (3×30 ml) to give 8.6 g of the salt. A sample was dissolved in a 1:1 mixture of 1 M HCl and ethyl acetate. The organic layer was separated, concentrated to dryness and analysed by chiral HPLC. This showed 98.2% of the "correct" (R)-enantiomer. From the mother liquor more material crystallised, which was filtered, washed and dried. This gave another 1.6 g of the salt. The free (R)-mandelic acid was analysed by HPLC (for suitable methodology, see Example 11A) and contained 99.0% of the "correct" enantiomer.

TABLE 2

| Example no. | mmol MA[1] | mmol PA | Eq. PA | EtOAc (ml) | Water (ml) | Water/EtOAc (%) | mmol MA/ml water-EtOAc | e.e. (%) |
|---|---|---|---|---|---|---|---|---|
| 4 | 5.96 | 2.9 | 0.49 | 3.7 | 0.30 | 7.5 | 1.61 | 99.2 |
| 5 | 10.45 | 5.1 | 0.49 | 6.4 | 0.52 | 7.5 | 1.51 | 98.9 |
| 6 | 93.30 | 42.0 | 0.45 | 54.5 | 5.50 | 9.2 | 1.40 | 98.7 |
| 7 | 155.31 | 77.7 | 0.50 | 91.5 | 10.20 | 10.0 | 1.53 | 99.0 |
| 8 | 76800 | 38400 | 0.50 | 66800 | 4600 | 6.4 | 1.08 | 98.2 |
| 9[2] | 42240 | 21120 | 0.50 | 33000 | 2500 | 7.0 | 1.19 | 99.6 |

MA = racemic mandelic acid derivative 3-chloro,5-difluoro-methoxy mandelic acid.
PA = (D)-proline amide.
Eq. PA = Amount of equivalents of proline amide compared to racemic mandelic acid derivative
EtOAc = ethyl acetate in ml.
Water/EtOAc (%) = concentration of water in ethyl acetate.
mmol MA/ml water-EtOAc = concentration range of racemic mandelic acid derivative per ml of ethyl acetate and water.
e.e. (%) = enantiomeric excess defined as the % mole fraction denoting the enantiomers in a mixture.
[1]Corrected for purity, i.e. initially 85-90% pure racemic mandelic acid derivative.
[2]The suspension was allowed to cool to 18° C. over 4 hours.

EXAMPLE 10

The racemic mandelic acid derivative 3-chloro,5-difluoromethoxy mandelic acid (0.2 g, 0.79 mmol) and (L)-proline amide (0.05 g, 0.48 mmol, 0.6 eq,) were added to 1 ml dioxane and the mixture heated to 90° C. During heat-up a thick suspension was formed. The suspension was filtered and (S)-mandelic acid liberated by extractive work up using 1 M HCl and ethyl acetate. 0.05 g enantiomer of ee: 92% was obtained.

EXAMPLE 11

Racemisation Procedure

Once the desired ("right") mandelic acid/prolinamide (MAPA) salt has been isolated by filtration, the mother liquors containing an excess of the other ("wrong") mandelic acid enantiomer (and also some unprecipitated prolinamide salt of the "right" mandelic acid) may be racemised—see racemisation scheme below. The resulting racemate may again be used in the process of the invention to isolate more of the desired enantiomer. This racemisation/recycling process may be repeated a number of times to obtain higher yields of the desired enantiomer, for example two recycles may permit up to 70% overall yield of the "right" mandelic acid, and three recycles may permit up to 80% yield.

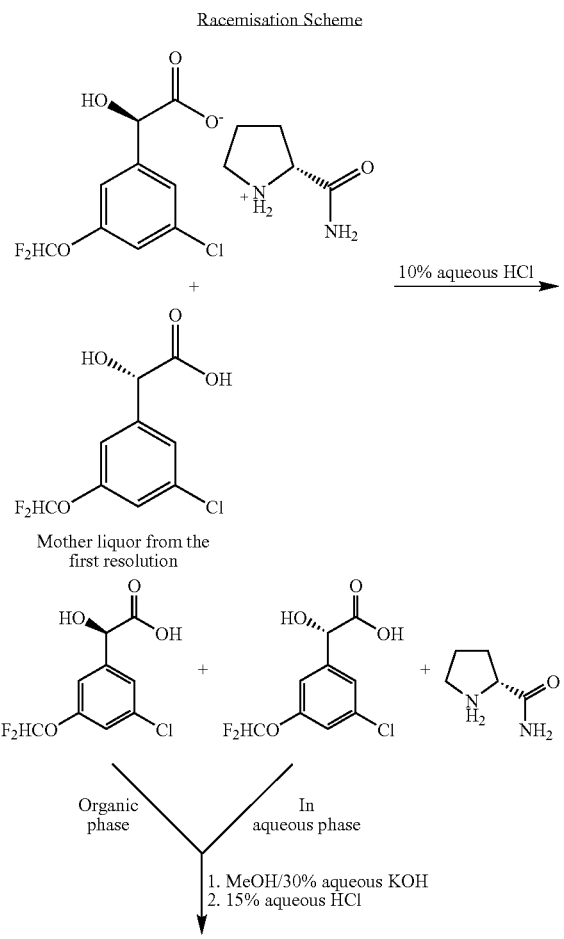

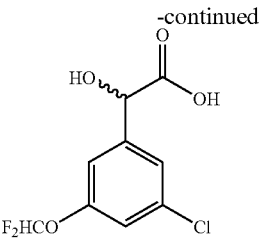

EXAMPLE 11A

Racemisation of Mother Liquor

The mother liquor, in ethyl acetate, from the resolution process (for example, from any of Examples 1-9 above), containing the "wrong" mandelic acid enantiomer in excess (3.35 kg, 3.53 L, corresponds to 0.462 kg mandelic acid, 1.83 mol) was concentrated under reduced pressure at 50-55° C. to a volume of 2.78 L. The solution was extracted at 15-25° C. with 10% aqueous hydrochloric acid (0.62 kg, 1.69 mol, 0.92 eq) to remove D-prolinamide. The organic solution was washed with deionised water (0.58 kg) after which phase inversion occurred with the organic phase below the aqueous phase. Sodium chloride (0.030 kg) was added to invert the phases again and the phases were separated. The organic phase was washed with 8.7% aqueous NaHCO$_3$ (0.71 kg, 0.74 mol, 0.40 eq). The organic phase was concentrated as much as possible under reduced pressure at 50-60° C. The remaining residue (0.483 kg) had a chemical purity of 76.5% as determined by HPLC and an optical purity for the S-enantiomer of 81% as determined by chiral HPLC. The residue was dissolved in methanol (1.33 kg, 1.67 L) and 30% aqueous potassium hydroxide (0.84 kg, 4.46 mol, 2.43 eq) was added at 25-40° C. The mixture was heated to 68-75° C. and stirred for approximately 3.5 hours until complete racemisation had occurred according to chiral HPLC. Methanol was distilled off under reduced pressure at 40-50° C. Dichloromethane (1.35 kg, 1.02 L) and water (0.20 kg) were added to the aqueous solution and the mixture was cooled to 0-5° C. 20% Aqueous hydrochloric acid (1.17 kg, 1.10 L, 6.41 mol, 3.50 eq) was added within 20 minutes to the stirred two-phase mixture at T=0-20° C. (exothermic reaction, pH=1). The mixture was stirred over a period of about 10 minutes at 20-25° C. until the precipitated oily product was dissolved completely in dichloromethane. The phases were separated and the aqueous solution was extracted with dichloromethane (0.53 kg, 0.40 L). The combined organic phases were washed with water (0.48 kg) and concentrated under reduced pressure at 40-50° C. This gave 0.443 kg of an oily product with a HPLC purity of 97.1 area %.

The HPLC conditions used for determination of the purity of the MAPA salt by HPLC were:

| | |
|---|---|
| Column: | Symmetry Shield RP8, 2.1 × 50 mm, 3.5 μm, Waters |
| Flow rate: | 0.5 mL/min. |
| Detection: | UV, 220 nm |
| Volume injection: | 15 μL |
| Temperature column: | 20° C. |
| "Running time": | 35 min.; Post time: 5 min. |
| Mobile phase: | A: 50 mL acetonitrile + 200 mL ammonium dihydrogenphosphate buffer + 750 mL pure water |

-continued

| Gradient: | B: 800 mL acetonitrile (HPLC-grade) + 200 mL ammonium dihydrogenphosphate buffer | | |
|---|---|---|---|
| | Time (min) | % Phase A | % Phase B |
| | 0 | 90 | 10 |
| | 5 | 90 | 10 |
| | 30 | 10 | 90 |
| | 35 | 2 | 98 |

The HPLC conditions used for determination of the optical purity of the MAPA salt by HPLC were:

| | |
|---|---|
| Column: | Chiralpak AD, 250 × 4.6 mm, DAICEL |
| Flow rate: | 1.0 mL/min |
| Detection: | UV, 215 nm |
| Volume injection: | 10 µL |
| Temperature column: | 20° C. |
| "Running time": | 30 min |
| Mobile phase: | n-Hexane/2-propanol/trifluoroacetic acid = 900 mL/100 mL/1 mL |

The resulting racemate may again be used in the process of the invention to isolate more of the desired enantiomer, for example according to the following Example.

EXAMPLE 11B

Resolution of the Mandelic Acid Obtained after Racemisation

A solution of the racemic mandelic acid (obtained after the first racemisation) in ethyl acetate (1.433 kg of a 29.9% (w/w) solution, 0.429 kg racemic mandelic acid, 1.698 mol, 1.00 eq) was filtered and added within 30 minutes to a stirred solution of D-prolinamide (0.095 kg, 0.853 mol, 0.49 eq) in ethyl acetate (0.407 kg, 0.452 L) as well as water (0.153 kg) at 72-75° C. After the addition was completed a clear solution was obtained. The mixture was cooled to 58° C. within 45 min. No crystallisation was observed. The mixture was cooled further to 0-2° C. within 2.5 hours. The salt started to precipitate at approximately 55° C. After stirring for a further hour at 0-2° C., the solid was filtered off and washed twice with a pre-cooled (0-5° C.) mixture of ethyl acetate/water=9:1 (w/w, 2×0.20 kg). A wet, off-white powder (0.264 kg) was obtained in 99.3% purity and 97.6% optical purity.

If necessary, the optical purity can be further improved by slurrying the product with ethyl acetate/water and filtering. For example, the optical purity can be improved further by the following re-work procedure.

EXAMPLE 11C

Re-work Procedure

The wet mandelic acid D-prolinamide salt (0.264 kg) was suspended in a mixture of ethyl acetate (1.00 kg, 1.11 L) and water (0.10 kg). The suspension was heated to 73-75° C. and stirred for 30 minutes at this temperature. The suspension was cooled to 3-5° C. within 2 hours and then stirred for another hour at this temperature. The solid was filtered off and washed twice with a pre-cooled (0-5° C.) mixture of ethyl acetate/water=9:1 (w/w, 2×0.38 kg). The white solid was dried under reduced pressure (10 mbar) at 35-40° C. until the mandelic acid.D-prolinamide salt had constant weight. This gave 0.225 kg of product (73.9%, based on D-prolinamide) with a chemical purity of >99% and optical purity of >99%.

This racemisation-resolution procedure can be repeated, for example twice. Furthermore, the D- or L-prolinamide may be recycled using conventional extraction techniques.

EXAMPLE 12

Different Salts

Once the mandelic acid enantiomers are separated then the desired enantiomer can be isolated as a different salt suitable for further processing. Depending which mandelic acid enantiomer is required, such a different salt may be isolated either from the prolinamide salt, or from the mother liquors remaining after the prolinamide salt has been filtered off.

Thus, for example, (R)-3-chloro,5-difluoro-methoxy mandelic acid.D-prolinamide salt may be isolated and then converted into a different salt for further processing. The mother liquors can then be racemised for recycling, for example as described before.

Alternatively, (S)-3-chloro,5-difluoro-methoxy mandelic acid.L-prolinamide salt may be isolated and then a different salt of (R)-3-chloro,5-difluoro-methoxy mandelic acid isolated from the mother liquors. The (S)-3-chloro,5-difluoro-methoxy mandelic acid.L-prolinamide salt may then be used for racemisation and recycling.

(R)-3-chloro,5-difluoro-methoxy mandelic acid ((2R)-[3-chloro-5-(difluoromethoxy)-phenyl](hydroxy)acetic acid) is a useful intermediate, but the free acid compound has a low melting point (52° C.) and is hard to crystallise. Furthermore, (R)-3-chloro,5-difluoro-methoxy mandelic acid is very soluble compared to the unsubstituted mandelic acid. As mentioned earlier, although 3-chloro,5-difluoro-methoxy mandelic acid is capable of forming salts with, for example, α,α-diphenyl-D-prolinole, such salts are not satisfactory for large-scale manufacturing purposes (having low yield and low enantiomeric excess).

The Examples above describe the isolation of, for example, (R)-3-chloro,5-difluoro-methoxy mandelic acid from a racemic mixture by resolution with D-prolinamide. These cyclic amide resolving salts are expensive, and thus cheaper salts are of further interest to permit even more efficient large-scale manufacturing.

We now provide further new salts of our substituted mandelic acids (of formula I) as a further feature of the invention. The discovery of such salts provides an efficient, inexpensive isolation of our mandelic acids as a solid, thereby creating opportunities for economic enantioselective processes and for improvements of the process using resolution with, for example, D-prolinamide.

Enantioselective routes to (R)-3-chloro,5-difluoro-methoxy mandelic acid are also of interest, and in such cases an efficient, inexpensive salt of the mandelic acid is attractive. Preferably the salt should be crystalline, enhance the enantiomeric purity upon formation and be directly useable in a subsequent (coupling) reaction.

The Examples below describe the preparation of certain metal salts of (R)-3-chloro,5-difluoro-methoxy mandelic acid (calcium, zinc and magnesium salts). Also described is the preparation of certain amine salts of (R)-3-chloro,5-difluoro-methoxy mandelic acid (i.e. the salts formed with 4-hydroxy-2,2,6,6-tetramethylpiperidine, triethanolamine, piperazine, 1,4-dimethylpiperazine, 2,4,6-trimethylpyridine and 4-hydroxy-1,2,2,6,6-pentamethylpiperidine.

EXAMPLE 12A

Ca, Zn and Mg salts of (R)-3-chloro,5-difluoro-methoxy mandelic acid

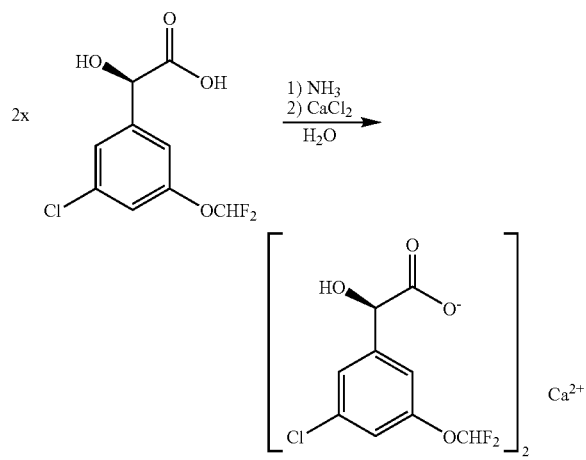

Calcium Salt

To a suspension of 0.449 g (1.778 mmol) of the (R)-mandelic acid (prepared from the (R)-MA-(D)-PA salt using HCl (aq), and water washing) in water (2.5 ml) was added a 25% w/w ammonia solution in water (0.133 g, 1.956 mmol, 1.1 eq), with a water transfer wash (0.15 ml). To the resulting solution was added a solution of 0.118 g (1.067 mmol. 0.6 eq) of calcium chloride in 0.7 ml of water, with a water transfer wash (0.1 ml). A solid was formed immediately. After 1 hour at ambient temperature, the mixture was cooled with an ice-bath and kept at 0° C. for 2 hours. Then, the suspension was filtered and the solid material washed twice with ice-cold water (2×0.9 ml). The compound was dried at 40° C. under vacuum to give 0.37 g (0.681 mmol, 76.6%) of the crystalline calcium salt (as confirmed by XRPD—as described hereinafter).

The procedure can also be performed with calcium acetate in place of calcium chloride.

Magnesium and Zinc Salts

Crystalline magnesium and zinc salts (as confirmed by XRPD—as described hereinafter) were obtained using an analogous procedure to that described for the calcium salt. The (R)-mandelic acid.Mg salt was obtained in 16% yield (MP=186° C.) and the (R)-mandelic acid.Zn salt was obtained in 78% yield.

In a further experiment, the Mg salt of a racemic 3-chloro, 5-difluoro-methoxy mandelic acid was obtained (75% yield), using an analogous procedure to that described above, by addition of 0.6 eq of magnesium hydroxide to a suspension to the racemic mandelic acid in water. The salt was obtained as a crystalline solid (as confirmed by XRPD), with a melting point of 113° C.

EXAMPLE 12B

Amine Salts of (R)-3-chloro,5-difluoro-methoxy mandelic acid

EXAMPLE 12B-1

Triethanolamine Salt

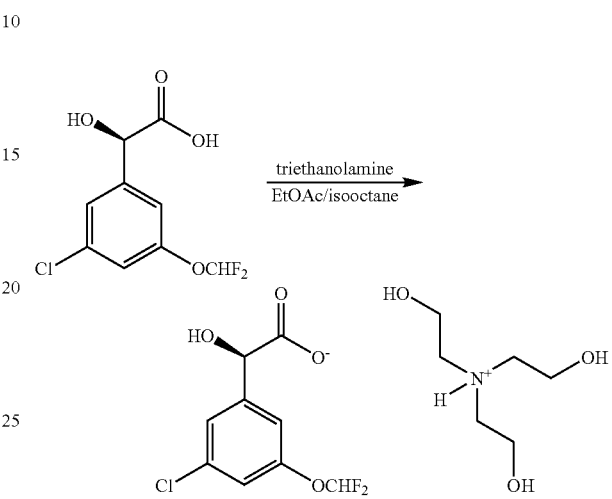

Triethanolamine (211.8 µl, 1.564 mmol) was added to a 0.356 M solution of the (R)-mandelic acid (0.359 g, 1.422 mmol; prepared from the (R)-MA-(D)-PA salt using HCl(aq), and water washing) in ethyl acetate at ambient temperature. The addition was accompanied by a weak exotherm. The solution was heated to 66° C. and isooctane added until the solution started to turn cloudy. The solution was cooled slowly to ambient temperature overnight. The solution was then cooled to 0° C. and the salt precipitated after 1½ hours stirring at 0° C. The suspension was stored in the refrigerator overnight, filtered, washed with EtOAc/isooctane 1.46:1 (2×1.23 ml), then vacuum dried at 40° C. to give 0.500 g (1.244 mmol, 88%) of the crystalline (R)-3-chloro,5-difluoro-methoxy mandelic acid.triethanolamine salt (melting-point (MP)=68° C.).

The crystallinity of the triethanolamine salt of the (R)-mandelic acid was confirmed by DSC (endotherm onset=68° C.) and XRPD. The following XRPD d-values and intensities were obtained:

| d-value (Å) | Relative intensity |
|---|---|
| 7.3 | m |
| 6.9 | m |
| 6.1 | s |
| 5.6 | vs |
| 5.4 | m |
| 5.2 | m |
| 4.60 | m |
| 4.45 | m |
| 4.33 | m |
| 4.11 | m |
| 3.80 | s |
| 3.72 | vs |
| 3.64 | s |
| 3.59 | m |
| 3.48 | m |
| 3.46 | m |
| 3.35 | m |

-continued

| d-value (Å) | Relative intensity |
|---|---|
| 3.31 | m |
| 3.24 | m |
| 3.09 | m |
| 3.05 | m |
| 2.92 | m |
| 2.79 | m |
| 2.60 | m |

The main, reproducible peaks have been tabulated using the following definitions.

| | |
|---|---|
| vs (very strong): | >50% rel. int. |
| s (strong: | 28-50% rel. int. |
| m (medium): | 9-28% rel. int. |
| w (weak): | 4-9% rel. int. |
| vw (very weak): | <4% rel. int. |

The relative intensities are derived from diffractograms measured with variable slits.

X-ray powder diffraction analysis (XRPD) was performed on samples prepared according to standard methods, for example those described in Giacovazzo, C. et al (1995), Fundamentals of Crystallography, Oxford University Press; Jenkins, R. and Snyder, R. L. (1996), Introduction to X-Ray Powder Diffractometry, John Wiley & Sons, New York; Bunn, C. W. (1948), Chemical Crystallography, Clarendon Press, London; or Klug, H. P. & Alexander, L. E. (1974), X-ray Diffraction Procedures, John Wiley and Sons, New York. X-ray analyses were performed using a PANalytical X'Pert PRO MPD diffractometer. The sample was analysed with, and without, internal reference. The measured peak values were adjusted and thereafter calculated into d-values.

Differential scanning calorimetry (DSC) was performed using a PerkinElmer DSC7 instrument, according to standard methods, for example those described in Höhne, G. W. H. et al (1996), Differential Scanning Calorimetry, Springer, Berlin. DSC onset temperatures may vary in the range ±5° C. (e.g. ±2° C.), and XRPD distance values may vary in the range ±2 on the last given decimal place.

EXAMPLE 12B-2

Other Amine Salts

Crystalline solid salts of (R)-3-chloro,5-difluoro-methoxy mandelic acid with 4-hydroxy-2,2,6,6-tetramethylpiperidine (MP=153° C.), piperazine (MP=135° C.), 1,4-dimethylpiperazine (MP=93° C.), 2,4,6-trimethylpyridine (MP=66° C.) and 4-hydroxy-1,2,2,6,6-pentamethylpiperidine (MP=145° C.) were obtained in an analogous way to Example 12B-1.

The crystallinity of the above amine salts of the (R)-mandelic acid was confirmed by XRPD as described herein.

The above amine salts may be formed with the single (R)- or (S)-enantiomer, or with a racemate of 3-chloro,5-difluoro-methoxy mandelic acid. For example, solid salts of a racemate of 3-chloro,5-difluoro-methoxy mandelic acid were obtained by an analogous procedure to that described above with 4-hydroxy-2,2,6,6-tetramethylpiperidine, triethanolamine (crystalline, MP=53° C.), 2,4,6-trimethylpyridine (crystalline, MP=72° C.) and 4-hydroxy-1,2,2,6,6-pentamethylpiperidine (crystalline, MP=120° C.).

The dicyclohexylamine salt of a racemate of 3-chloro,5-difluoro-methoxy mandelic acid was obtained by an analogous procedure to that described above (but dicyclohexylamine salts of single MA enantiomers were not obtained).

EXAMPLE 12C

Enantiomeric Selectivity of the Conglomerate Triethanolamine Salt

The triethanolamine salt of 3-chloro-5-difluoromethoxy mandelic acid is particularly interesting as it occurs as a crystalline conglomerate. This makes it possible to improve the enantiomeric excess of (R)-3-chloro,5-difluoro-methoxy mandelic acid as product from an enantioselective process.

There is a distinct difference between a conglomerate and a racemic compound. Looking at a 50:50 mixture of both enantiomers, a conglomerate consists of a mixture of crystals of the two enantiomers in equal amounts. Although in bulk the conglomerate is optically neutral, the individual crystals contain only the R or S-enantiomer. This is in contrast to a racemic compound where the individual crystals contain equal amounts of both enantiomers and the racemic crystals form a perfectly ordered array of R and S molecules. Racemic compounds and conglomerates can be distinguished by determination of their melting point diagrams (phase diagrams) or by using powder X-ray diffraction or solid state IR spectroscopy; the data of pure enantiomers are identical with the data of the conglomerate, but different from that of a racemic compound.

For the triethanolamine salt of 3-chloro-5-difluoromethoxy mandelic acid, being a conglomerate makes it possible to isolate the triethanolamine salt of the (R)-mandelic acid from an enantiomerically enriched mixture of the mandelic acid by direct crystallisation. The maximum theoretical yield can be calculated by: 100-100×(amount of the wrong enantiomer present in the sample+same amount of the desired enantiomer)/total amount of solid. For example, starting with 95% w/w of the desired enantiomer, the maximum yield is 90%. Starting with 90% w/w of the desired enantiomer, the maximum yield is 80%, etc. (R)-3-chloro-5-difluoromethoxymandelic acid with an e.e. of 90% can, for example, be the product of an enantioselective process.

EXAMPLE 12C-1

Racemic 3-chloro-5-difluoromethoxy mandelic acid (51.25 mg, 0.203 mmol) was added to a 0.351 M solution of the (R)-mandelic acid (0.607 g, 2.405 mmol; prepared from the (R)-MA-(D)-PA salt using HCl(aq), and water washing) in ethyl acetate at ambient temperature. The enantiomeric excess of the (R)-mandelic acid in the solution was determined to be 92.4% by chiral HPLC analysis (performed as in Example 11 above). Triethanolamine (0.417 g, 2.739 mmol) was added to the solution at 23° C. The temperature rose to 25° C. upon the addition. The solution was heated to 70° C. At 70° C., isooctane (1.5 ml) was added and the solution was seeded with a few granules of the triethanolamine salt of (R)-3-chloro-5-difluoromethoxy mandelic acid (99.8% ee; see Example 12B). The solution was cooled to 65° C. and since crystallization had not started the seeding was repeated. The solution was cooled to 26° C. over 3 hours, but as there was still no precipitation of the salt, the solution was heated again to 70° C., seeded and then allowed to cool. Finally, the crystallization started at 58° C. after another seeding. The suspension was cooled to ambient temperature and left to stir overnight. A sample was filtered off the next morning, the optical purity of which was determined to be 98.1% ee by chiral HPLC analysis (see Example 11). The bulk of the suspension was cooled to, and stirred at 1° C. for 2¼ hours. The salt was isolated by filtration, washed with EtOAc/isooctane 2.5:1 (2×2.07 ml) and vacuum dried at 40° C. overnight to give the triethanolamine salt of (R)-3-chloro-5-difluoromethoxy mandelic acid as a white powder (0.897 g, 88.8%). The optical purity of the salt was determined to be 99.5% ee by chiral HPLC analysis (see Example 11).

EXAMPLE 12C-2

Racemic 3-chloro-5-difluoromethoxy mandelic acid (371.29 mg, 1.470 mmol) was added to a 0.351 M solution of (R)-mandelic acid (3.500 g, 13.856 mmol; prepared from the (R)-MA-(D)-PA salt using HCl(aq), and water washing) in ethyl acetate at ambient temperature. The enantiomeric excess of (R)-mandelic acid in the solution was determined to be 91.1% by chiral HPLC analysis (see Example 11). Triethanolamine (2.566 g, 16.856 mmol) was added to the solution at 23° C. The temperature rose to 29° C. upon the addition. The solution was heated to 70° C. At 70° C. isooctane (8.6 ml) was added and the solution was seeded with a few granules of the triethanolamine salt of (R)-3-chloro-5-difluoromethoxy mandelic acid (99.8% ee; see Example 12B). The solution was cooled to 65° C. and since crystallization had not started the seeding was repeated. The solution was cooled by stages and seeded four more times. Finally at about 40° C. the salt crystallized. The suspension was cooled to room temperature and left to stir overnight. A sample was filtered off the next morning, the optical purity of which was determined to be 97.0% ee by chiral HPLC analysis (see Example 11). The bulk of the suspension was cooled to and stirred at 1° C. for 2¾ hours. The salt was isolated by filtration, washed with EtOAc/isooctane 4:1 (2×7.5 ml) and vacuum dried at 40° C. overnight to give the triethanolamine salt of (R)-3-chloro-5-difluoromethoxy mandelic acid as a white powder (5.451 g, 92.0%). The optical purity of the salt was determined to be 98.7% ee by chiral HPLC analysis (see Example 11).

It is to be noted that any of the salts described herein may be in the form of polymorphs, solvates or hydrates, and such forms are also covered by the invention. Also covered by the invention are any tautomers of the mandelic acid derivatives described herein.

The invention claimed is:

1. A (R)/(D) or (S)/(L) mandelic acid/cyclic amide salt having the formula IIb

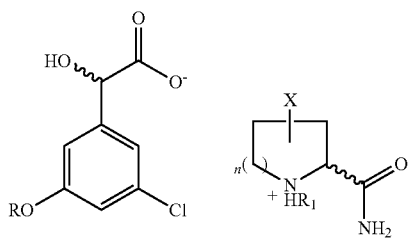

IIb wherein
R is selected from the group consisting of $CHF_2$, H, $C_{1-6}$ alkyl, $CH_2F$, $CHCl_2$ and $CClF_2$;
n is 0, 1 or 2;
$R_1$ is H or $C_{1-6}$ alkyl; and
X is H, halo or $C_{1-6}$ alkyl.

2. The (R)/(D) mandelic acid/cyclic amide salt according to claim 1, which is of formula VI

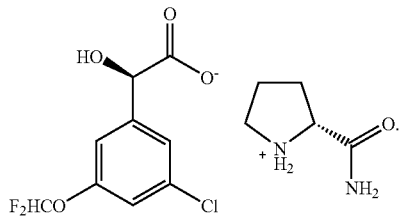

VI

3. A metal salt of a mandelic acid of formula Ia

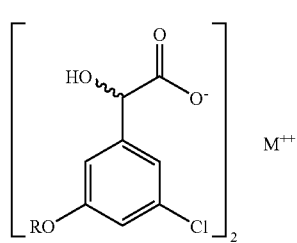

Ia wherein
R is selected from the group consisting of $CHF_2$, H, $C_{1-6}$ alkyl, $CH_2F$, $CHCl_2$ and $CClF_2$; and
M is a metal ion selected from the group consisting of calcium, zinc and magnesium.

4. The metal salt, according to claim 3, wherein the mandelic acid of formula Ia is the (R)-mandelic acid or the (S)-mandelic acid.

5. An amine salt of a mandelic acid of formula Ib

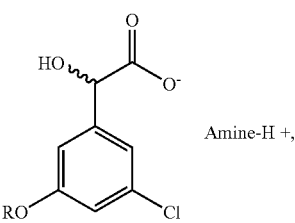

Ib wherein
R is selected from the group consisting of $CHF_2$, H, $C_{1-6}$alkyl, $CH_2F$, $CHCl_2$ and $CClF_2$; and
the amine is selected from the group consisting of triethanolamine, 4-hydroxy-2,2,6,6-tetramethylpiperidine, piperazine, 1,4-dimethylpiperazine, 2,4,6-trimethylpyridine, 4-hydroxy-1,2,2,6,6-pentamethylpiperidine and dicyclohexylamine.

6. The amine salt according to claim 5,
wherein
the mandelic acid of formula Ib is the (R)- or (S)-mandelic acid, and
the amine is selected from the group consisting of triethanolamine, 4-hydroxy-2,2,6,6-tetramethylpiperidine, piperazine, 1,4-dimethylpiperazine, 2,4,6-trimethylpyridine and 4-hydroxy-1,2,2,6,6-pentamethylpiperidine.

7. The amine salt according to claim 5 or claim 6, wherein the mandelic acid of formula Ib is the (R)-mandelic acid, and the amine is triethanolamine.

8. The salt according to any one of claims 1, 3 and 5 wherein the mandelic acid is (R)-3-chloro-5-difluoro-methoxy mandelic acid ((2R)[3-chloro-5-(difluoromethoxy) phenyl]-(hydroxy)acetic acid).

* * * * *